United States Patent [19]

Steigerwald

[11] Patent Number: 4,457,487

[45] Date of Patent: Jul. 3, 1984

[54] FLUSHING DEVICE

[75] Inventor: Carl J. Steigerwald, Wauconda, Ill.

[73] Assignee: The Kendall Company, Boston, Mass.

[21] Appl. No.: 391,193

[22] Filed: Jun. 23, 1982

[51] Int. Cl.³ .............................................. F16K 1/32
[52] U.S. Cl. .................................... 251/117; 137/605;
137/DIG. 4; 251/339; 604/249
[58] Field of Search ................ 128/675; 251/117, 339;
604/33, 34, 249, 250; 137/DIG. 4, 605

[56] References Cited

U.S. PATENT DOCUMENTS

| | | |
|---|---|---|
| 3,675,891 | 7/1972 | Reynolds et al. .................... 251/117 |
| 4,200,119 | 4/1980 | Cunningham ..................... 25/117 X |
| 4,291,702 | 9/1981 | Cole ..................................... 128/675 |

Primary Examiner—Dalton L. Truluck
Attorney, Agent, or Firm—Powell L. Sprunger

[57] ABSTRACT

A flushing device comprising, a housing having an inlet, an outlet, a cavity communicating between the inlet and outlet and defining an annular valve seat, and an opening communicating with the cavity, with the valve seat facing away from the opening. The device has an elastic valve element received in the cavity with an annular valve portion sealingly engaged against the seat. The valve element has a stem extending through the opening and the stem sealingly engages against the portion of the housing defining the opening. The valve element has a passageway extending therethrough and communicating between the inlet and the outlet, and the device has a relatively large channel communicating between the inlet and seat and between the seat and outlet. The device has an insert extending across the passageway and having a relatively small bore.

3 Claims, 4 Drawing Figures

FLUSHING DEVICE

BACKGROUND OF THE INVENTION

The present invention relates to flushing devices.

During certain medical procedures it is desirable to measure the pressure in the heart. In order to accomplish this result, the distal end of a cardiac catheter is centrally placed in the right side of the heart. It is desirable to prevent blood clots from forming in the catheter, so a heparinized saline solution is slowly passed through the catheter, such as a rate of 3 cubic centimeters per hour. Occasionally, it is desirable to withdraw a blood sample from the catheter. After this has been accomplished, it is desirable to flush the residual blood from the catheter to prevent the catheter from clotting shut. In order to accomplish this result, the catheter is flushed with the saline solution at a relatively fast rate after a blood sample has been taken.

An assortment of devices has been proposed to accomplish flushing, but the devices have been relatively complex, and many require two hands for operation.

SUMMARY OF THE INVENTION

A principal feature of the present invention is the provision of an improved flushing device of simplified construction.

The flushing device of the present invention comprises, a housing having an inlet, an outlet, a cavity communicating between the inlet and outlet and defining an annular valve seat, and an opening communicating with the cavity, with the valve seat facing away from the opening. The device has an elastic valve element received in the cavity with an annular valve portion sealingly engaged against the seat. The valve element has a stem extending through the opening and means on the stem for sealingly engaging against the portion of the housing defining the opening. The valve element has a passageway means extending therethrough and communicating between the inlet and the outlet. The device has relatively large channel means communicating between the inlet and seat and between the seat and outlet. The device has an insert extending across the passageway means and having a relatively small bore.

A feature of the present invention is that the valve element is normally located at a first position with the valve portion sealingly engaged against the seat.

Another feature of the invention is that the valve element obstructs passage of fluid through the channel means in the first position of the valve element, and the fluid passes at a relatively low rate through the bore insert.

Yet another feature of the invention is that in the first position of the valve element the stem means sealingly engages against the housing to prevent passage of fluid through the housing opening.

Another feature of the invention is that the valve element may be moved to a second flushing position with the valve portion spaced from the seat.

Yet another feature of the invention is that when the valve element is at the second position the device permits a fast flow or flushing of fluid through the channel means and past the seat.

A further feature of the invention is that in the second position of the valve element the stem means sealingly engages against the housing to prevent passage of fluid through the opening.

Still another feature of the invention is that the valve element may be moved from the first to second position by pressing the stem toward the housing.

Yet another feature of the invention is that the valve element may be operated through use of only one hand.

Further features will become more fully apparent in the following description of the embodiments of this invention and from the appended claims.

DESCRIPTION OF THE PREFERRED EMBODIMENTS

Figure 1:
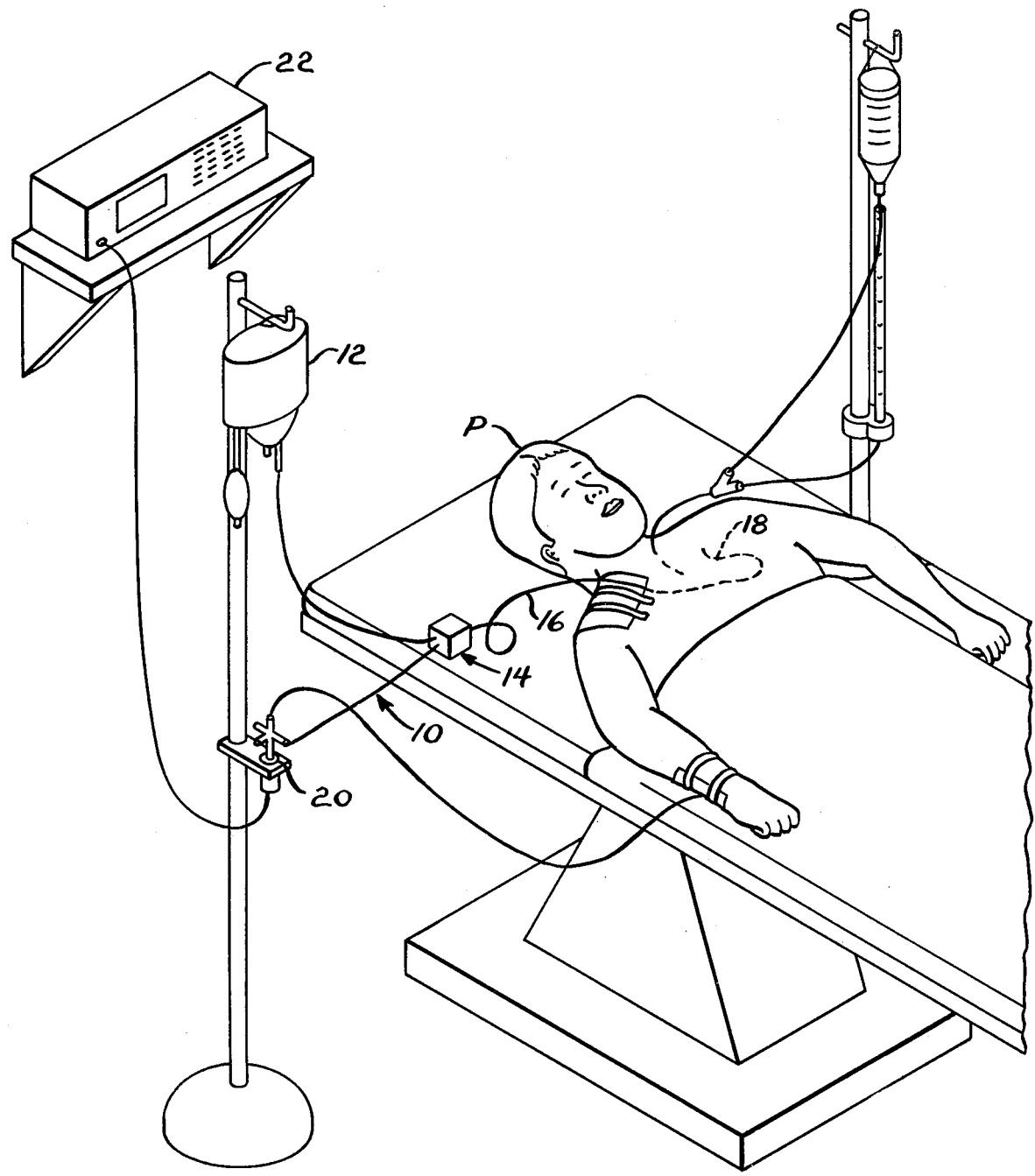
FIG. 1 is a perspective view of an intravenous system including the flushing device of the present invention for a patient.

Referring now to FIG. 1, there is shown an intravenous system generally designated 10 comprising a source 12 of intravenous fluid, such as heparinized saline solution, which is connected to a flushing device 14 which normally permits a relatively slow flow of the saline solution through the device 14, such as 3 cubic centimeters per hour, into a cardiac catheter 16 which is connected to the flushing device 14 and has a distal end 18 centrally placed in the right side of the heart of a patient P. The flushing device 14 is connected to a pressure transducer 20 which in turn is connected to suitable electronic equipment 22 to indicate the pressure in the patient's heart.

Figure 2:
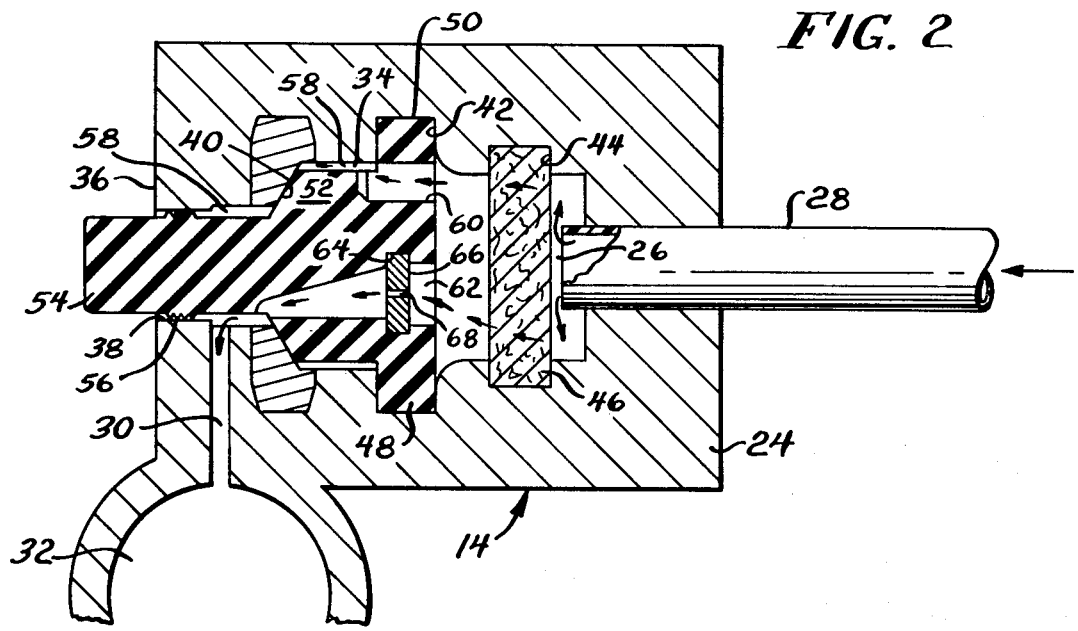
FIG. 2 is a sectional view of the flushing device with a valve element in a first closed position.
Figure 4:
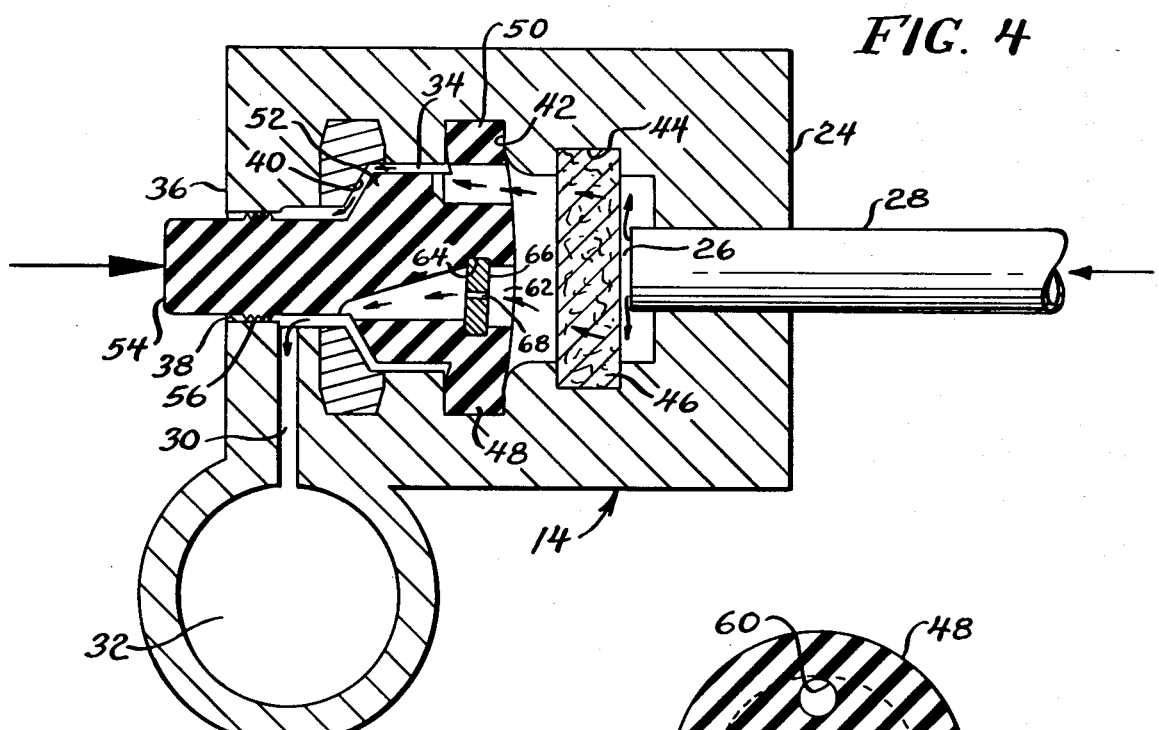
FIG. 4 is a sectional view of the flushing device with the valve element in a second open position.
Figure 3:
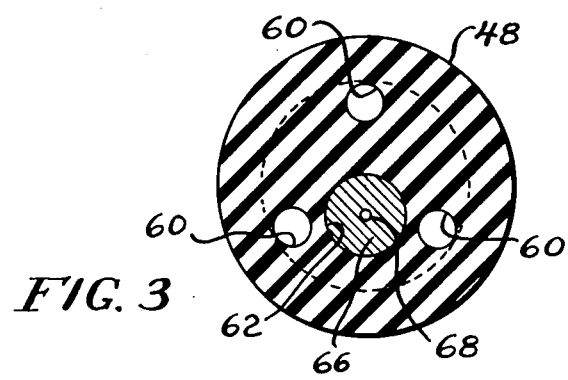
FIG. 3 is a sectional view of the valve element.

A flushing device 14 of the present invention is illustrated in FIGS. 2–4. The flushing device 14 has a housing 24 which may be constructed of a suitable plastic material. The housing 24 has an inlet 26 communicating with a tube 28 which is connected to the source 12 of liquid. The housing 24 has an outlet 30 which communicates through an opening 32 with the cardiac catheter 16 leading to the patient and the pressure transducer 20. The housing 24 also has a cavity 34 which communicates between the inlet 26 and outlet 30. The housing 24 has a generally cylindrical portion 36 defining an opening 38 communicating with the cavity 34, and the housing 24 defines an annular valve seat 40 in the cavity 34 facing away from the opening 38. The housing 24 also has first and second spaced annular grooves 42 and 44, respectively, for a purpose which will be described below.

The device 14 has a cylindrical filter element 46 retained in the groove 44. The filter element 46 removes debris from the liquid as it passes from the inlet 26 to the outlet 30. The filter element 46 may be constructed from a suitable material, such as sintered polyethylene.

The device 14 also has a valve element 48 which may be constructed from a suitable elastic material, such as silicone rubber. The valve element 48 has an annular flange 50 retained in the groove 42 to hold the valve element 48 in place. The valve element 48 also has an annular valve portion 52 sealingly engaged against the seat 40. The valve element 48 has a stem 54 extending from the cavity 34 through the opening 38, with the stem 54 having a plurality of annular rings 56 extending around the stem 54 and sealingly engaged against the cylindrical portion 36 of the housing 24.

The housing 24 and valve element 48 define one or more relatively large channels 58 communicating with the inlet 26 through one or more apertures 60 in the valve element 48, with the channels 58 communicating between the inlet 26 and the seat 40, and between the seat 40 and the outlet 30.

The valve element 48 has a passageway 62 extending therethrough and communicating between the inlet 26 and the outlet 30. The valve element 48 has an annular groove 64 located in the passageway 62.

The device 14 has a cylindrical insert 66 which may be made of a suitable plastic material. The insert has a relatively small bore 68 such as 0.002 to 0.003 inches in diameter. As shown, the insert 66 is received in the groove 64, such that the insert 66 extends across the passageway 62.

In use, with reference to FIG. 2, the valve element 48 is normally located in the first sealing position with the valve portion 52 sealingly engaged against the seat 40 in order to prevent passage of liquid through the channels 58. Accordingly, the liquid normally passes through the filter element 46 into the passageway 62 and through the bore 68 of the insert 66 at a relatively slow rate, such as 3 cubic centimeters per hour to the outlet 30 and to the patient.

When it is desirable to flush the catheter and permit a relatively fast flow of liquid into the catheter, with reference to FIG. 4, the stem 54 of the valve element 48 is pressed toward the housing 24 in order to move the valve element 48 to a second open position with the valve portion 52 spaced from the seat 40. In this configuration, the liquid passes at a relatively fast rate through the channels 58 between the inlet 26 and outlet 30 in order to flush the catheter. After flushing has been completed, the stem 54 of the valve element 48 is released, and the valve element 48 flexes to its first sealing position with the valve portion 52 sealingly engaged against the seat 40 in order to again obstruct passage of liquid through the passageway 62 to the catheter.

The operation of the valve element 48 may be accomplished through use of one hand. Also, it will be noted in FIGS. 2 and 4 that in both first and second positions of the valve element, the rings 56 sealingly engage against the cylindrical portion 36 of the housing 24, and prevent passage of liquid from the cavity 34 through the opening 38.

The foregoing detailed description is given for clearness of understanding only, and no unnecessary limitations should be understood therefrom, as modifications will be obvious to those skilled in the art.

I claim:

1. A flushing device, comprising:

a housing having an inlet, an outlet, a cavity communicating between the inlet and outlet and defining an annular valve seat, an opening communicating with the cavity, with the valve seat facing away from the opening;

an elastic valve element consisting of resilient material received in the cavity with an annular valve portion sealingly engaged against the seat, said valve element having a stem of one-piece construction with the valve portion extending through the opening and means on the stem for sealingly engaging against the portion of the housing defining the opening, said valve element having passageway means extending therethrough and communicating between the inlet and outlet, said device having relatively large channel means communicating between the inlet and seat and between the seat and outlet; and an insert extending across the passageway means and having a relatively small bore, said valve element being movable between a normal first position with the valve portion sealingly engaged against the seat to obstruct passage of fluid through the channel means, with fluid passing at a slow rate through the insert bore, and with the stem means sealingly engaging against the housing to prevent passage of fluid through the opening, and a second flushing position by pressing the stem toward the housing, with the valve portion spaced from the seat to permit a fast flow of fluid through the channel means and past the seat, and with the stem means sealingly engaging against the housing to prevent passage of fluid through the opening.

2. The device of claim 1 wherein the stem engaging means comprises a plurality of annular rings extending around the stem.

3. The device of claim 1 including a filter element extending across the cavity.

* * * * *

UNITED STATES PATENT AND TRADEMARK OFFICE
CERTIFICATE OF CORRECTION

PATENT NO. : 4,457,487
DATED : July 3, 1984
INVENTOR(S) : Carl J. Steigerwald

It is certified that error appears in the above-identified patent and that said Letters Patent are hereby corrected as shown below:

In column 3, line 42, after "the" (1st occurrence) insert --channels 58 and cause relatively slow passage of liquid through the--.

Signed and Sealed this

Eleventh Day of December 1984

[SEAL]

Attest:

GERALD J. MOSSINGHOFF

Attesting Officer

Commissioner of Patents and Trademarks